United States Patent [19]

Pelz et al.

[11] 4,062,851

[45] Dec. 13, 1977

[54] PROCESS FOR THE RESOLUTION OF CERTAIN OCTAHYDROBENZOCYCLOHEPTAPYRIDOISOQUINOLINOLS

[75] Inventors: Karel Pelz, St. Laurent; Francois T. Bruderlein, Montreal; Leslie G. Humber, Dollard des Ormeaux, all of Canada

[73] Assignee: Ayerst McKenna and Harrison Ltd., Montreal, Canada

[21] Appl. No.: 635,993

[22] Filed: Nov. 26, 1975

[51] Int. Cl.$^2$ .................................... C07D 471/06
[52] U.S. Cl. ........................... 260/289 C; 260/286 R; 260/288 CF; 260/DIG. 8
[58] Field of Search ............ 260/288 CF, 284, 289 C, 260/286 R, 283 RF, DIG. 8

[56] References Cited

U.S. PATENT DOCUMENTS

| | | | |
|---|---|---|---|
| 2,545,094 | 3/1951 | Long et al. | 260/DIG. 8 |
| 2,545,095 | 3/1951 | Long et al. | 260/DIG. 8 |
| 2,680,135 | 6/1954 | Gregory | 260/DIG. 8 |
| 3,852,452 | 12/1974 | Bruderlein et al. | 260/283 S |
| 3,914,305 | 10/1975 | Bruderlein et al. | 260/343 |
| 3,985,751 | 10/1976 | Bruderlein et al. | 260/283 R |

FOREIGN PATENT DOCUMENTS

| | | | |
|---|---|---|---|
| 167,345 | 5/1954 | Australia | 260/DIG. 8 |

Primary Examiner—Donald G. Daus
Assistant Examiner—Mary C. Vaughn
Attorney, Agent, or Firm—Stephen Venetianer

[57] ABSTRACT

An efficient, commercially feasible process for the resolution of the organic bases, (±)-(4a,13b-trans)-(3-hydroxy,13b-trans)-3-isopropyl-2,3,4,4a,8,9,13b,14-octahydro-1H-benzo[6,7]cyclohepta[1,2,-3-de)-pyrido[2,1-a]isoquinolin-3-ol and (±)-(4a,13b-trans)-(3-hydroxy,13b-trans)-3-tert-butyl-2,3,4,4a,8,9,13b,14-octahydro-1H-benzo[6,7]cyclohepta[1,2,3-de]-pyrido[2,1-a]isoquinolin-3-ol, known neuroleptic agents, is disclosed. The process comprises resolving the racemic organic bases with L-(+)-tartaric acid to obtain directly the pure L-(+) tartrate of the (+)-enantiomer and converting the latter salt to the corresponding (+)-enantiomer free base.

4 Claims, No Drawings

PROCESS FOR THE RESOLUTION OF CERTAIN OCTAHYDROBENZOCYCLOHEP-TAPYRIDOISOQUINOLINOLS

BACKGROUND OF THE DISCLOSURE a. Field of Invention

This invention relates to a process for the optical resolution of the racemic organic bases, (±)-(4a,13b-trans)-(3-hydroxy,13b-trans)-3-isopropyl-2,3,4,4a,8,9,13b,14-octahydro-1H-benzo[6,7]cyclohepta[1,2,3-de]-pyrido[2,1-a]isoquinolin-3-ol and (±)-(4a,13b-trans)-(3-hydroxy,13b-trans)-3-tert-butyl-2,3,4,4a,8,9,13b,14-octahydro-1H-benzo[6,7]cyclohepta[1,2,3-de]pyrido[2,1-a]isoquinolin-3-ol into their corresponding (+)-enantiomers.

b. Prior Art

For convenience, (4a,13b-trans)-(3-hydroxy,13b-trans)-3-isopropyl-2,3,4,4a,8,9,13b,14-octahydro-1H-benzo[6,7]cyclohepta[1,2,3-de]-pyrido[2,1-a]isoquinolin-3-ol is hereafter designated as Compound I and (4a,13b-trans)-(3-hydroxy,13b-trans)-3-tert-butyl-2,3,4,4a,8,9,13b,14-octahydro-1H-benzo[6,7]cyclohepta[1,2,3-de]pyrido[2,1-a]isoquinolin-3-ol is hereafter designated as Compound II.

Compounds I and II are neuroleptic agents with essentially all the activity residing in the (+)-optically active enantiomer. The racemic form of Compound II is known generically as "butaclamol", see L. G. Humber and F. Bruderlein, Abstracts of Papers of the 167th Am. Chem. Soc. Meeting, Los Angeles, California, Division of Medicinal Chemistry, Paper No. 5; Apr. 1–5, 1974; and K. Voith, ibid (Paper No. 6). The (+)-form of Compound I is known generically as "dexclamol". The preparation of the racemic mixture of Compounds I and II is described in U.S. Pat. No. 3,914,305, issued Oct. 21, 1975 and U.S. Pat. No. 3,852,452 issued Dec. 3, 1974; see also Belgian Pat. No. 762,595, issued Aug. 5, 1971. In these Patents Compounds I and II are recited as 5-isopropyl-and 5-tert-butyl-1,4,5,6,6a,10,11,15-b-octahydro-3H-benzo[6,7]cyclohepta[1,2,3-de]-pyrido[2,1-a]isoquinolin-5-ol (Isomer A), respectively. Compounds I and II are described in U.S. patent application U.S. No. 518,853, filed Oct. 29, 1974, now U.S. Pat. No. 3,985,751.

Prior to the present disclosure the resolution of racemic organic bases was usually performed by procedures requiring several steps of multiple recrystallizations. Because of time and expense required for such procedures, the need for an efficient resolution of the above noted racemic organic bases, Compounds I and II, is highly desirable.

Accordingly, a process is described here which avoids multiple recrystallizations and resolves the above noted bases in a commercially feasible operation and in high yield.

DESCRIPTION OF THE INVENTION

The process for resolving racemic Compound I and Compound II comprises: dissolving one part by weight of a racemic mixture of the Compound I or Compound II and 1.0 to 1.3 parts by weight of L-(+)-tartaric acid in 4 to 6 parts by volume of methanol at 20° to 40° C: diluting the solution with 1 to 3 parts by volume of acetone or ether at 15° to 25° C to crystallize the corresponding L-(+)-tartrate of the (+) enantiomer of the compound; dissolving one part by weight of the L-(+)-tartrate in a mixture of 5 to 8 parts by volume of water and 5 to 8 parts by volume of a water-immiscible organic solvent containing 5 to 10 parts by weight of alkali; separating the water-immiscible solvent from the aqueous phase; isolating the corresponding (+)-enantiomer free base from the water immiscible solvent; and if desired converting said (+)-enantiomer free base into its corresponding pharmaceutically acceptable salt.

Preferred water-immiscible organic solvents for the process include toluene and benzene.

Respecting the alkali, any alkali may be used for the present process provided that it will render basic the aqueous phase and cleave the L-(+)-tartrate of the (+)-enantiomer and cause the (+)-enantiomer free base to go into the water-immiscible solvent. Preferred alkalies for this purpose include ammonium hydroxide, the alkali metal hydroxides, for example, sodium or potassium hydroxide, the alkaline earth hydroxides, for example, calcium or magnesium hydroxide, or sodium or potassium carbonate.

Noteworthy about the present process is that fact that the L-(+)-tartrate of the (+)-enantiomer of the compound of formula I is obtained pure by direct crystallization from the first step of this process and that further purification of this salt by recrystallization is not required. Furthermore, if the (+)-enantiomer free base is converted to a pharmaceutically acceptable salt, preferably the hydrochloride, one recrystallization of the latter salt is sufficient to obtain the pure, pharmaceutically acceptable salt of the (+)-enantiomer. All these features avoid the expensive and tedious operations of purification procedure usually required for resolution and serve to promote the efficiency of the present process.

The following example illustrates further this invention.

EXAMPLE I a. Resolution

Racemic Compound I hydrochloride (2890 g., 7.52 mole) is suspended in toluene (14.5 l., 5 parts) and converted to its corresponding free base by stirring with concentrated ammonium hydroxide (1170 ml., 1.2 equivalents) and water (585 ml.). The clear aqueous phase is discarded. The toluene layer is washed with water (1170 ml.), dried over sodium sulfate and concentrated under reduced pressure to give the free base of racemic Compound I as a thick oil. The oil is dissolved in methanol (11.6 l., 4 parts) at 40° C, solid L-(+)-tartaric acid (1.13 kg., 7.52 mole) is added and the mixture is stirred until a solution is obtained. The solution is diluted with acetone (2890 ml., 1 part) and allowed to crystallize for 1 hour. More acetone (2890 ml., 1 part) is added. The mixture is cooled to 20° C and stirred for another hour. The crystals are collected by filtration and washed with methanol-acetone 50/50 (2 × 2.17 l.) and then with acetone (2.17 l.). The L-(+)-tartrate of the (+)-enantiomer of Compound I thus obtained forms pale straw coarse crystals, 870 g. air-dried (crop A, 46.4% of the theoretical amount of the (+)-enantiomer tartrate), m.p. 180° –187° C (decompn.), $[\alpha]_D^{25} = +200°$ (c = 1% in methanol). The mother liquor from the crystallization is processed as described in section (b) hereinafter.

b. Recycling of material recovered from the mother liquor

The mother liquor from section (a) is concentrated to a small volume. Toluene (16.1) is added and the tartrate salt is converted to the free base by stirring with concentrated ammonium hydroxide (2 l.) and water (2 l.). The clear aqueous phase is discarded. The toluene layer is washed with water (2 l.), dried over sodium sulfate and evaporated under reduced pressure. The residual oil (about 3.7 kg., containing theoretically 2.04 kg. of base) is dissolved in isopropanol (5 parts, 10 l.), heated to 50° C and concentrated hydrochloric acid (560 ml.) is added in one portion. The crystals of racemic Compound I hydrochloride separate almost immediately. The mixture is stirred for 30 minutes at 55° C. Acetone (2 parts, 4.0 l.) is added and the mixture cooled to 20° C over a period of 90 minutes, the crystals are collected by filtration, washed with isopropanol-acetone (5:2. 2.0 l.) and sucked as dry as possible. The wet cake is removed from the filter, slurried in the latter solvent mixture (3.7 l.), filtered and washed with acetone (1.86 l.). The acetone-wet cake of the racemic Compound I hydrochloride (wet weight 2.4 kg.) is used without drying for subsequent resolution as described above. Dry weight estimated by drying of an aliquot is 1240 g., $[\alpha]_D^{25} = -2°$, (c = 1% in methanol), m.p. 266.5° -268° C (decomp.).

The mother liquor which contains the (−)-enantiomer is discarded. The racemic hydrochloride, obtained above, is converted to its free base and subjected to the resolution procedure as described in section (a). From 1240 g. of the (±)-hydrochloride 385 g. of the L-(+)-tartrate of the (+)-enantiomer are obtained, called crop B, (m.p. 179°–187° C decomp.), $[\alpha]_D^{25} = +199°$ (c = 1% in methanol).

The mother liquor from the preceding recycling procedure is subjected to a further recycling. Thus crop C (161 g.) of the L-(+)-tartrate of the (+)-enantiomer is obtained m.p. 178 –183.5° C (decompn.) $[\alpha]_D^{25} = +203°$ (c = 1% in methanol).

The mother liquor from the second recycling procedure is subjected to a further recycling procedure giving crop D (64 g.) of the L-(+)-tartrate of the (+)-enantiomer, m.p. 179.5°–185° C (decompn.) $[\alpha]_D^{25} = +202°$ (c = 1% in methanol).

Total yield of the L-(+)-tartrate of the (+)-enantiomer of Compound I (crops A+B+C+D) is 1480 g. (870 g. + 385 g. + 161 g. + 64 g. respectively), which is 93% of the theoretical yield. The four crops are combined and converted directly without further purification to the (+)-hydrochloride as follows.

c. Conversion of the L-(+)-tartrate of the (+)-enantiomer of Compound I to the corresponding (+)-enantiomer hydrochloride The combined L-(+)-tartrate fractions of the (+)-enantiomer (1480 g., 1.75 mole) are suspended in toluene (6 parts, 8.9 l.) and converted to the corresponding free base by stirring with concentrated ammonium hydroxide (910 ml., 7 mole) and water (910 ml.). The clear aqueous phase is discarded. The toluene solution is washed with water (910 ml.), dried over sodium sulfate and evaporated under reduced pressure to dryness. The residual oil is dissolved in methylene chloride (3 parts, 4.5 l.) and hydrogen chloride is passed into the stirred solution until the solution has pH2. The solvent is evaporated under reduced pressure removing in part excess hydrogen chloride. The residual oil is redissolved in methylene chloride (3 parts, 4.5 l.) and the solution is diluted at reflux temperature with ethyl acetate (3 parts, 4.5 l.). Methylene chloride (2.25 l., 1.5 parts) is removed by distillation at atmospheric pressure (bath temperature, 67°–70° C). The mixture is cooled to room temperature, stirred for an additional hour and crystals are collected by filtration. The cake is washed with 30% methylene chloride in ethyl acetate (2 × 740 ml.) and with ethyl acetate (740 ml.). The (+)-enantiomer hydrochloride obtained weighs 1180 g. (air-dried, 87.5%) m.p. 241°–241.5° C (decompn.), $[\alpha]_D^{25} = +213°$ (c = 1% in methanol).

d. Final purification of Compound I (+)-enantiomer hydrochloride

The (+)-enantiomer hydrochloride, obtained above (1180 g.), is dissolved in 2.5 parts methylene chloride (2.95 l.) and charcoal (Nuchar) (60 g., 5%) is added to the solution. The mixture is stirred for 10 minutes and filtered through diatomaceous earth (Celite). The filter pad of diatomaceous earth is washed with methylene chloride (590 ml.). The filtrate is heated to reflux and ethyl acetate (2.36 l.) is added slowly in such a way that it mixes with methylene chloride returning from a condenser of the reflux system in order to prevent precipitation of oily product (30 minutes). The solution is seeded and about 1200 ml. of methylene chloride is removed by distillation at atmospheric pressure while the product crystallizes. The mixture is cooled to room temperature and stirred for an additional hour. The crystals are collected by filtration, washed with 30% methylene chloride in ethyl acetate (2 × 590 ml.) and with ethyl acetate (590 ml.). The pure (+)-enantiomer hydrochloride of compound I is dried for 5 hours at 60° C in a vacuum oven. Yield: 1070 g. (90.6% for the purification), m.p. 241° C (decompn.), $[\alpha]_D^{25} = +215°$ (c = 1% in methanol).

In the same manner Compound II is resolved into its corresponding (+)-enantiomer, the corresponding hydrochloride of the (+)-enantiomer having m.p. 288°–291° C, $[\alpha]_D^{25} = +218.5°$ (c = 1% in methanol).

We claim:

1. A process for resolving (±)-(4a,13b-trans)-(3-hydroxy,13b-trans)-3-isopropyl-2,3,4,4a,8,9,13b,14-octahydro-1H-benzo[6,7]cyclohepta[1,2,3-de]-pyrido[2,1-a]isoquinolin-3-ol and (±)-(4a,13b-trans)-(3-hydroxy,13b-trans)-3-tert-butyl-2,3,4,4a,8,9,13b14-octahydro-1H-benzo[6,7]cyclohepta[1,2,3-de]-pyrido[2,1-a]isoquinolin-3-ol, which consists of dissolving one part by weight of a racemic mixture of the (±)-(4a,13b-trans)-(3-hydroxy,13b-trans)-3-isopropyl-2,3,4,4a,8,9,13b,14-octahydro-1H-benzo[6,7]cyclohepta[1,2,3-de]pyrido[2,1-a]isoquinolin-3-ol or (±)-(4a,13b-trans)-(3-hydroxy,13b-trans)-3-tert-butyl-2,3,4,4a,8,-9,13b,14-octahydro-1H-benzo[6,7]cyclohepta[1,2,3-de]pyrido[2,1-a]isoquinolin-3-ol and 1.0 to 1.3 parts by weight of L-(+)-tartaric acid in 4 to 6 parts by volume of methanol at 20° to 40° C, diluting the solution with 1 to 3 parts of volume of acetone or ether at 15° to 25° C to crystallize the corresponding L-(+)-tartrate of the (+)-enantiomer of the compound; dissolving one part by weight of the L-(+)-tartrate in a mixture of 5 to 8 parts by volume of water and 5 to 8 parts by volume of a water-immiscible organic solvent containing 5 to 10 parts by weight of alkali; separating the water-immiscible solvent from the aqueous phase, and isolating the corresponding (+)-enantiomer free base from the water-immiscible solvent.

2. The process of claim 1 in which the (+)-enantiomer free base is converted into its corresponding pharmaceutically acceptable salt.

3. The process of claim 1 in which the water-immiscible solvent is toluene or benzene.

4. The process of claim 1 in which the alkali is ammonium hydroxide, an alkali metal hydroxide or an alkali earth hydroxide, or sodium or potassium carbonate.

* * * * *